United States Patent
Chiang (10) Patent No.: US 10,842,398 B2
(45) Date of Patent: Nov. 24, 2020

(54) WIRELESS INTRACRANIAL PRESSURE MONITORS

(71) Applicant: Orion Biotech Inc., Taipei (TW)

(72) Inventor: Ming-Fu Chiang, Taipei (TW)

(73) Assignee: ORION BIOTECH INC., Taipei (TW)

( * ) Notice: Subject to any disclaimer, the term of this patent is extended or adjusted under 35 U.S.C. 154(b) by 522 days.

(21) Appl. No.: 15/390,494

(22) Filed: Dec. 24, 2016

(65) Prior Publication Data

US 2017/0273583 A1 Sep. 28, 2017

(30) Foreign Application Priority Data

Mar. 28, 2016 (TW) .............................. 105109684 A (51) Int. Cl.
*A61B 5/03* (2006.01)
*A61B 5/00* (2006.01)
*A61M 25/00* (2006.01)
*A61B 5/01* (2006.01)

(52) U.S. Cl.
CPC ............ *A61B 5/031* (2013.01); *A61B 5/6868* (2013.01); *A61B 5/0031* (2013.01); *A61B 5/01* (2013.01); *A61B 5/6852* (2013.01); *A61B 2562/0247* (2013.01); *A61M 2025/0002* (2013.01)

(58) Field of Classification Search
CPC ..... A61B 5/031; A61B 5/6868; A61B 5/6852; A61B 5/0031; A61B 2562/0247; A61M 2025/0002
See application file for complete search history.

(56) References Cited

U.S. PATENT DOCUMENTS

| | | | |
|---|---|---|---|
| 6,210,346 B1 * | 4/2001 | Hall ...................... | A61B 5/031 600/561 |
| 6,248,080 B1 | 6/2001 | Miesel et al. | |
| 6,537,232 B1 | 3/2003 | Kucharczyk et al. | |
| 7,785,268 B2 * | 8/2010 | Miethke ............... | A61B 5/0031 600/561 |
| 2002/0045921 A1 * | 4/2002 | Wolinsky ............. | A61B 5/0028 607/61 |
| 2008/0139959 A1 | 6/2008 | Miethke et al. | |
| 2010/0022896 A1 | 1/2010 | Yadav et al. | |
| 2011/0160609 A1 * | 6/2011 | Stone ....................... | A61B 3/16 600/561 |
| 2013/0247644 A1 | 9/2013 | Swoboda et al. | |
| 2014/0180239 A1 | 6/2014 | Mittermeyer et al. | |
| 2014/0210637 A1 * | 7/2014 | Gohler .................... | A61B 5/002 340/870.07 |
| 2014/0276180 A1 | 9/2014 | Dextradeur et al. | |

(Continued)

FOREIGN PATENT DOCUMENTS

CN 201101746 Y 8/2008
CN 101332082 A 12/2008

(Continued)

*Primary Examiner* — Devin B Henson
(74) *Attorney, Agent, or Firm* — Cheng-Ju Chiang (57) ABSTRACT

Wireless intracranial monitors are provided. The wireless intracranial monitors comprise a main body, a wireless transceiver, a processing module, and a sensing module, in which the sensing module contains a catheter. On the catheter, a pressure sensor is configured to detect deformation of the catheter or a diaphragm connected to the pressure sensor. The detected deformation is then transmitted to the processing module through an in-catheter wire.

10 Claims, 9 Drawing Sheets

(56) References Cited

U.S. PATENT DOCUMENTS

2015/0297103 A1    10/2015  Hu et al.
2016/0066803 A1     3/2016  Hu et al.
2018/0310848 A1*   11/2018  Tvedt ................... A61B 5/6885

FOREIGN PATENT DOCUMENTS

| | | |
|---|---|---|
| CN | 201333032 Y | 10/2009 |
| CN | 101621962 A | 1/2010 |
| CN | 101959448 A | 1/2011 |
| CN | 102159129 A | 8/2011 |
| CN | 202600616 U | 12/2012 |
| CN | 104352233 A | 2/2015 |
| CN | 104434081 A | 3/2015 |
| CN | 104665805 A | 6/2015 |
| CN | 204428024 U | 7/2015 |
| CN | 105125201 A | 12/2015 |
| CN | 105286847 A | 2/2016 |
| CN | 105407954 A | 3/2016 |
| DE | 102005020569 A1 | 11/2006 |
| DE | 102012221284 A1 | 5/2014 |
| EP | 1702641 A2 | 9/2006 |
| JP | H4-269938 A | 9/1992 |
| JP | 2008-539811 A | 11/2008 |
| JP | 4778040 B2 | 9/2011 |
| JP | 5301210 B2 | 9/2013 |
| JP | 5660901 B2 | 1/2015 |
| TW | 200522858 A | 7/2005 |
| WO | 91/05575 A1 | 5/1991 |
| WO | 2004/026129 A1 | 4/2004 |
| WO | 2012/078861 A3 | 6/2012 |
| WO | 2017/065881 A1 | 4/2017 |

* cited by examiner

FIG. 5

WIRELESS INTRACRANIAL PRESSURE MONITORS

CROSS-REFERENCE TO RELATED APPLICATION AND CLAIM OF PRIORITY

This application claims the benefit of Taiwan Patent Application No. 105109684, filed on Mar. 28, 2016, in the Taiwan Intellectual Property Office, the disclosure of which is incorporated herein in its entirety by reference.

1. Technical Field

At least one embodiment of the present invention relates to intracranial pressure (ICP) monitors. More particularly, at least one embodiment of the present invention relates to wireless ICP monitors.

2. Description of the Related Art

Intracranial pressure (ICP) is the pressure inside the skull. As intracerebral hemorrhage or intracranial tumors emerges, the intracranial pressure elevates in accordance with the increasing volume of these cranial constituents.

Intracranial hypertension usually leads to compression on multiple tissues, such as the brain stem and cerebellum. Accordingly, the monitoring of intracranial pressure is one important topic in the therapies to patients with encephalopathy, skull fracture, cranial tumors, or intracerebral hemorrhage.

The monitoring of intracranial pressure is an even more important topic in neurosurgery. One of the most damaging aspects of brain trauma and other conditions is an elevated intracranial pressure. The elevated intracranial pressure usually leads to secondary injuries such as obstruction of cerebral blood flow, cerebral hypoxia, and cerebral compression. In order to apply the decompression surgery on patients with intracranial hypertension in time, medical practitioners must carefully monitor variation of the intracranial pressure during the neurosurgery.

Another important topic commonly discussed in the operating room is the complex configuration of equipment, which physically interferes the operation and movement of surgeons. Here, the conventional intracranial pressure monitors are connected to hardware through physical wiring, which comes with more problems since any accidental movement of the ICP monitor inserted in intracranium may cause severe brain injuries to patients.

SUMMARY

At least one embodiment of the present invention provides a wireless intracranial monitors comprising a main body, a wireless transceiver, a processing module, and a sensing module.

The wireless transceiver is configured in the main body, in which the processing module is connected to the wireless transceiver and the sensing module respectively. Moreover, the sensing module comprises a catheter. In the catheter, a pressure sensor is configured to detect deformation, induced by external pressure, of the catheter or of a diaphragm connected to the pressure sensor. The detected deformation is then transmitted to the processing module through an in-catheter wire.

DESCRIPTION OF THE PREFERRED EMBODIMENTS

The examples depicted in the following section are provided for the purpose of detailed explanation of the features of preferred embodiments, in order to enable one having ordinary skill in the art to understand the preferred embodiments. It is to be understood that the specifications provided in the drawings are merely for the purposes of illustration and that various changes without departing from the spirit and intention may be included in the present invention.

Figure 1:
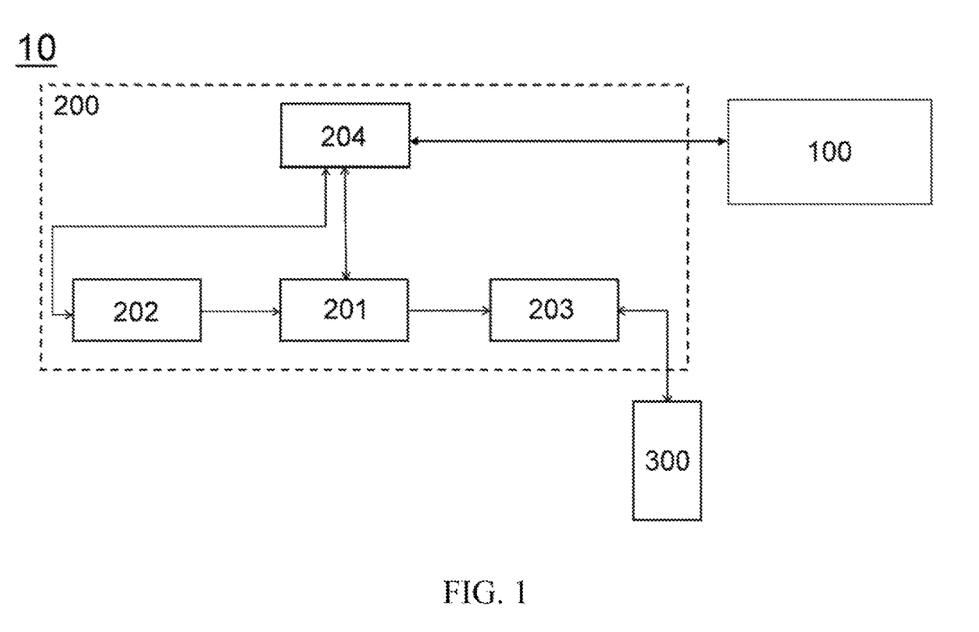
FIG. 1 is a block diagram illustrating a circuit, in accordance with some embodiments of the present invention.

FIG. 1 is a block diagram illustrating a circuit, in accordance with some embodiments of the present invention. As illustrated in FIG. 1, the wireless intracranial pressure monitor 10 comprises a main body 400 (shown in FIG. 3B and FIG. 4B), a wireless transceiver 100, a processing module 200, and a sensing module 300.

More particularly, the wireless transceiver 100 is configured in the main body 400. The wireless transceiver 100 in the present embodiments is a coil, in which the coil is a RF coil. The processing module 200 is connected to the wireless transceiver 100 and the sensing module 300 respectively.

Figure 2:
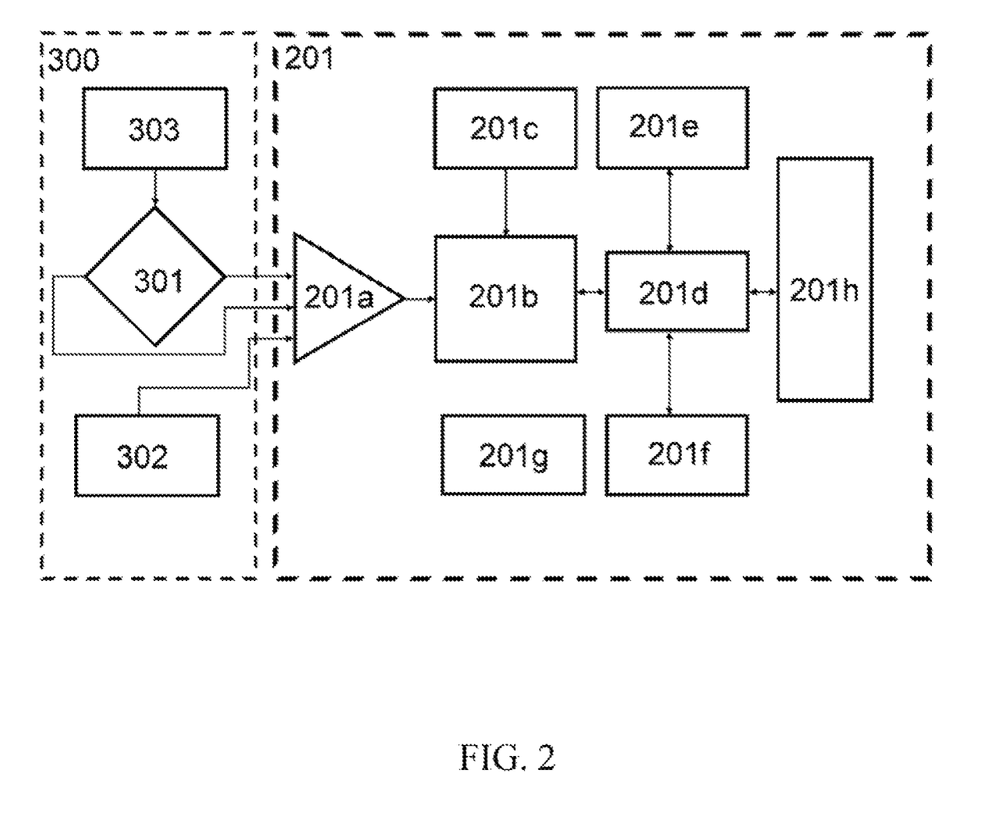
FIG. 2 is a block diagram illustrating a circuit, in accordance with some embodiments of the present invention.

Moreover, the processing module 200 comprises a microcontroller 201, a power supply 202, an analog front-end circuit 203, and an RF transceiver 204. The RF transceiver 204 is connected to the microcontroller 201, in which the power supply 202 is connected to the RF transceiver 204 and the microcontroller 201 respectively. The analog front-end circuit 203 may further comprise a programmable-gain amplifier 201a (as shown in FIG. 2), in which the analog front-end circuit 203 is configured to convert analog signals obtained by the sensing module 300 to digital signals. As such, the analog front-end circuit 203 is connected to the microcontroller 201 and the sensing module 300 respectively.

In FIG. 1, the power supply 202 provides power to the processing module 200 and the sensing module 300. In some embodiments of FIG. 1, the power supply 202, configured in the main body 400 of the wireless intracranial pressure monitor 10, is implemented as Li-ion batteries or rechargeable batteries. In some other embodiments of FIG. 1, the power supply 202 is implemented as a wireless charging module, transferring power through the interaction between the RF transceiver 204 and an RF reader, to provide power to the processing module 200 and the sensing module 300.

In some embodiments of FIG. 1, the analog front-end circuit 203 may be integrated with the microcontroller 201. For example, some embodiments of FIG. 1 comprise a microcontroller 201 having the ability as an analog-to-digital converter (ADC). Similar embodiments are illustrated in FIG. 2.

FIG. 2 is a block diagram illustrating a circuit, in accordance with some embodiments of the present invention. The differences between FIG. 1 and FIG. 2 are the implementation of the microcontroller 201 and the sensing module 300. More particularly, the embodiments in FIG. 2 comprises no analog front-end circuit 203, in which the analog front-end circuit 203 is replaced by a microcontroller 201 having the ability to perform same tasks as an analog front-end circuit. Accordingly, the microcontroller 201 is directly connected to the sensing module 300 in FIG. 2.

The microcontroller 201 in FIG. 2 comprises a programmable-gain amplifier (PGA) 201a, an analog-to-digital converter (ADC) 201b, an analog-to-digital buffer (ADC buffer) 201c, a digital signal processor (DSP) 201d, a power management oscillator (PMO) 201e, a digital register 201f, a power-on reset (POR) 201g, and an I²C/SPI interface 201h. In FIG. 2, the arrowheads indicate the directions of power flow or data flow between components.

The power-on reset 201g is configured in the microcontroller 201, in which the precise location of power-on reset may be varied based on the manufacturing processes. The programmable-gain amplifier 201a is connected to the sensing module 300 and the analog-to-digital converter 201b respectively, in which the analog-to-digital converter 201b is further connected to the analog-to-digital buffer 201c.

The digital signal processor 201d is connected to the analog-to-signal converter 201b, and the power management oscillator 201e is connected to the digital signal processor 201d and the power supply 202 respectively (shown in FIG. 1). On the other hand, the digital register 201f is connected to the digital signal processor 201d. After being converted, the digital signals are transferred through the connection between the digital signal processor 201d and the I²C/SPI interface 201h, in which the I²C/SPI interface 201h is connected to the wireless transceiver 204 (as shown in FIG. 1) and the digital signal processor 201d respectively.

The programmable-gain amplifier 201a receives analog signals from the sensing module 300. The analog signals are obtained by detecting and recording external factors, such as temperature or pressure, as voltages. Accordingly, the programmable-gain amplifier 201a may systematically amplify the analog signals then pass the analog signals to the analog-to-digital converter 201b.

In FIG. 2, the sensing module 300 comprises a sensing circuit 301, a temperature sensor 302, and a regulator 303. The programmable-gain amplifier 201a may connected to the sensing circuit 301 and the temperature sensor 302 respectively, and the regulator 303 is connected to the sensing circuit 301. In some embodiments, the sensing circuit 301 is a pressure sensing circuit and the regulator 303 is configured to regulate the sensitivity and other parameters of the sensing circuit 301. In some embodiments, the sensing circuit 301 may be other types of sensors.

In FIG. 2, the wireless intracranial pressure monitor comprises the temperature sensor 302 to simultaneously monitor the pressure and body temperature of a subject.

Figure 3A:
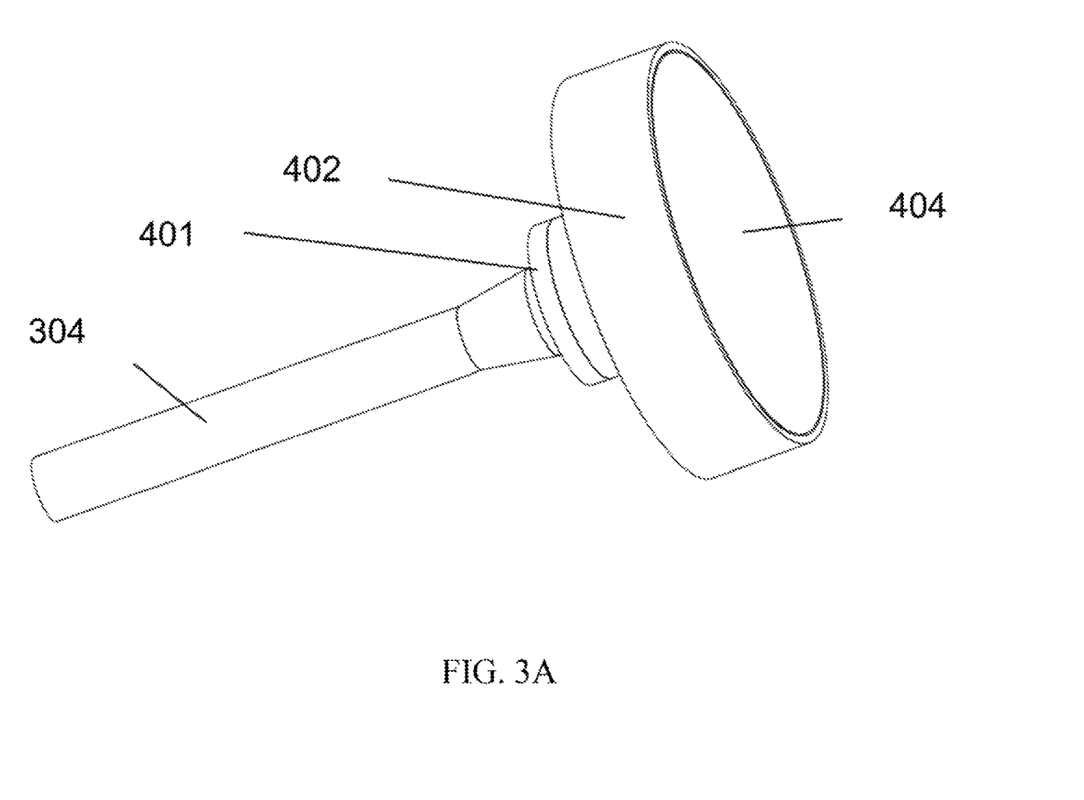
FIG. 3A is a perspective view illustrating some embodiments of the present invention.
Figure 3B:
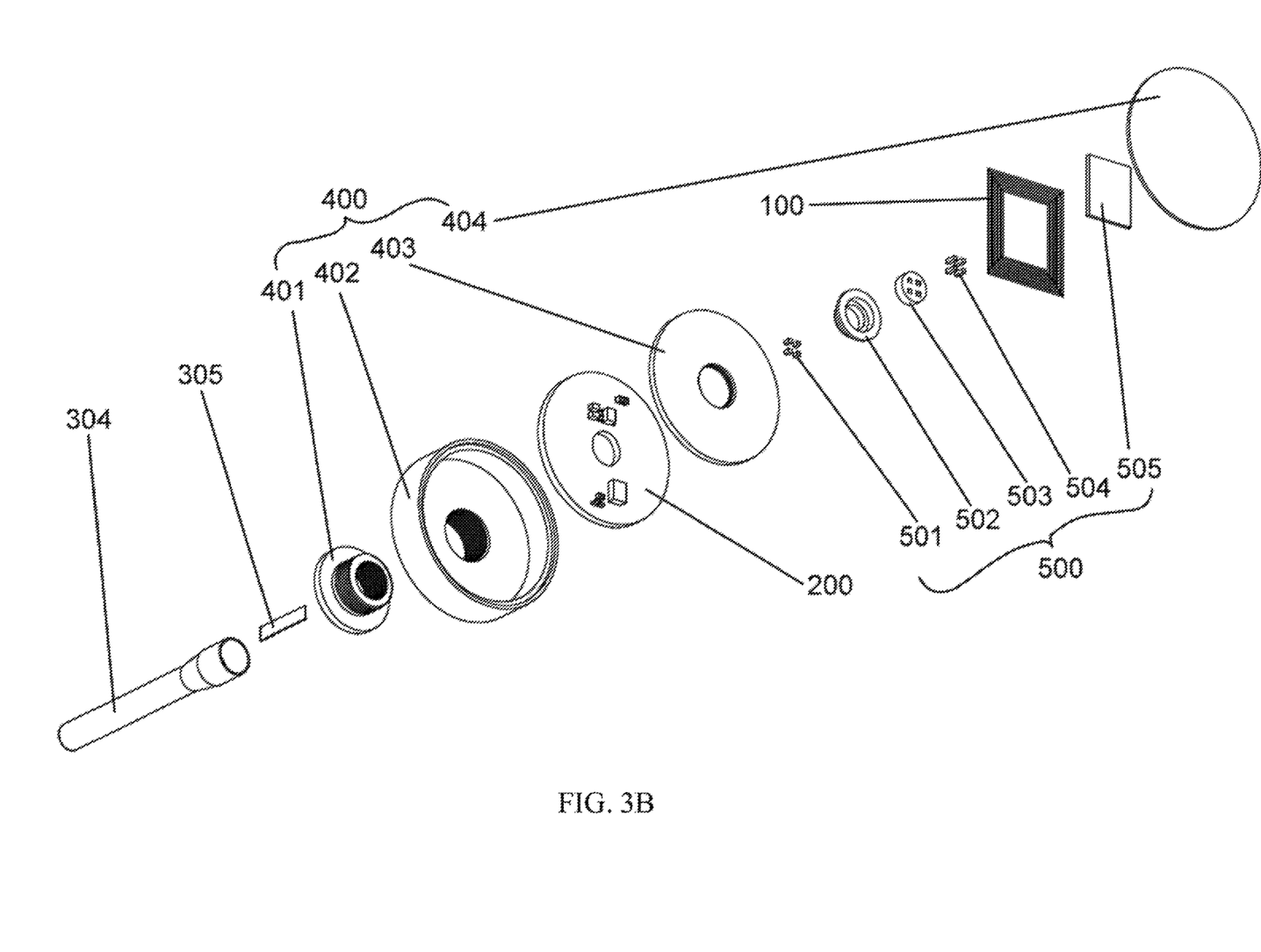
FIG. 3B is an exploded view illustrating some embodiments of the present invention.

Referring to FIG. 3A and FIG. 3B. FIG. 3A is a perspective view illustrating some embodiments of the present invention. FIG. 3B is an exploded view illustrating some embodiments of the present invention. As illustrated in FIG. 3A, the wireless intracranial pressure monitor 10 comprises an adapter 401, a housing 402, a cover 404, and a catheter 304. The adapter 401, the housing 402, and the cover 404 are part of the main body 400, as the catheter 304 is part of the sensing module 300.

Figure 3C:
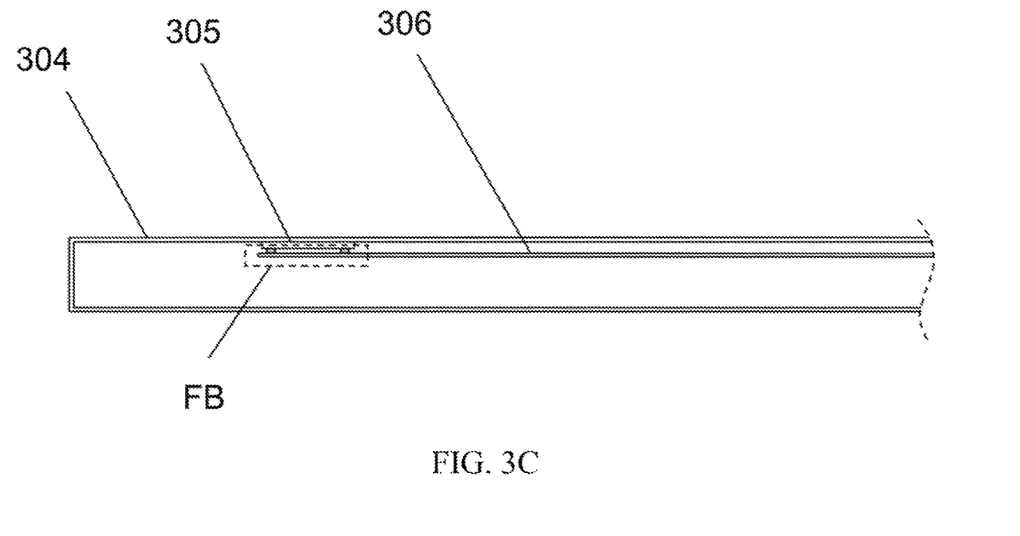
FIG. 3C is a horizontal cross-sectional view of a sensing module, in accordance with some embodiments of the present invention.

FIG. 3B is an exploded view of the wireless intracranial pressure monitor 10. The main components of the wireless intracranial pressure monitor 10 in FIG. 3B comprises a main body 400, a wireless transceiver 100, a processing module 200, and a sensing module 300. The sensing module 300 comprises the catheter 304, in which a pressure sensor 305 is configured on or configured in the catheter 304. In the present embodiments, the pressure sensor 305 is configured to detect deformation of the catheter 304 induced by pressure, as well as transfer the detected deformation to the processing module 200 through the in-catheter wire 306 (as shown in FIG. 3C).

In the present embodiments, the catheter 400 comprises an adapter 401, a housing 402, a spacer 403, and a cover 404. The adapter 401 is connected to the catheter 304 by screwing means in some embodiments, and the housing 402 is connected to the adapter 401. However, the catheter 304, the adapter 401, and the housing 402 may be made as a uni-body in some other embodiments.

The spacer 403 is configured in the housing 402 to separate the wireless transceiver 100 and the processing module 200. The wireless transceiver 100 is a coil (i.e., an RF coil) in some embodiments, but the wireless transceiver 100 may be any module having the ability to transfer data in a wireless network in some other embodiments.

In the present embodiments, the processing module 200 is a circular printed circuit board with a circular hole at the center. The circuitry may be embodied as illustrated in FIG. 1 or FIG. 2.

The connection between the cover 404 and the housing 402 encloses the wireless transceiver 100 and the processing module 200 in the wireless intracranial pressure monitor 10. Moreover, a connector 500 is configured in the housing 400 in the present embodiments to support the components and structure in the housing 400.

More particularly, the connector 500 comprises a first wire 501, a first supporter 502, a second supporter 503, a second wire 504, and a supporting plate 505. The first wire 501 is connected to the processing module 200, while the first supporter 502 is connected to the spacer 403 and the second supporter 503 respectively. The second wire 504, on the other hand, penetrates through the second supporter 503 and is connected to the first wire 501. Similarly, the supporting plates 505 are connected to the second wire 504 and the wireless transceiver 200 respectively.

The connector 500 having abilities to transfer power and data is optional in some other embodiments. In the present embodiments, the first wire 501 and the second wire 504 are metal wires to connect the processing module 200 and the wireless transceiver 100. The first supporter 502, the second supporter 503, and the supporting plate 505 are configured to provide mechanical support and electrical isolation to the processing module 200, the first wire 501, the second wire 504, and the wireless transceiver 100.

Figure 3D:
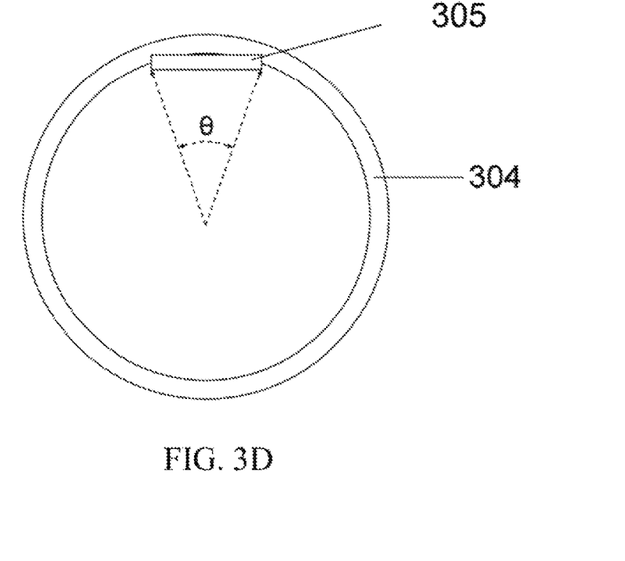
FIG. 3D is a vertical cross-sectional view of a sensing module, in accordance with some embodiments of the present invention.

Referring to FIG. 3C and FIG. 3D. FIG. 3C is a horizontal cross-sectional view of a sensing module, in accordance with some embodiments of the present invention. FIG. 3D is a vertical cross-sectional view of a sensing module, in accordance with some embodiments of the present invention. The catheter 304 in FIG. 3C is a circular tube. More particularly, the catheter 304 is a titanium alloy tube which is 2 mm in outside diameter, 1.5 mm in inside diameter, and 0.25 mm in wall thickness. The specification renders the catheter 304 able to slightly deform. The internal space of the catheter 304 is enclosed from the monitored region. The enclosure maintains the internal space of the catheter 304 at atmospheric pressure and thus creates a difference in pressure between the internal space and the monitored region.

As illustrated by the angle θ in FIG. 3D, the pressure sensor 305 is a semiconductor strain gauge attached to or embedded in the catheter 304 in the present embodiments. The angle θ at the center line of catheter 304 enclosed by two rays is 40°. Each of the two straight arrow lines representing the two rays shows the inside radius of the catheter 304. The pressure sensor 305 detects the radial deformation and circumferential deformation and converts the detected deformation into voltages with a bridge circuit. In the present embodiments, the in-catheter wire 306 is connected to the pressure sensor 305 attached on the catheter 304 to the sensing module 200 through a flip bump FB (enclosed by the dashed line). The in-catheter wire 306 provides a channel to transfer the voltage signal from the pressure sensor 305 to the processing module 200.

The specification (e.g., the length, shape, and material) of the pressure sensor 305 and the catheter 304 may be varied in some other embodiments in accordance with the applied region and targeted tissue. For example, the catheter 304 or the main body 400 may be coated with a layer of antimicrobial metals to avoid contamination and infection.

Figure 4A:
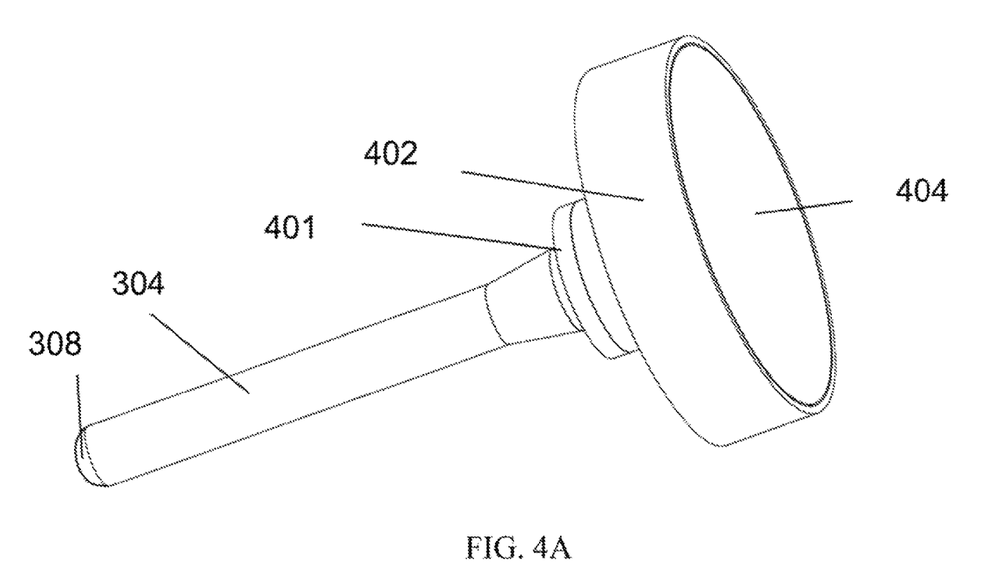
FIG. 4A is a perspective view illustrating some embodiments of the present invention.
Figure 4B:
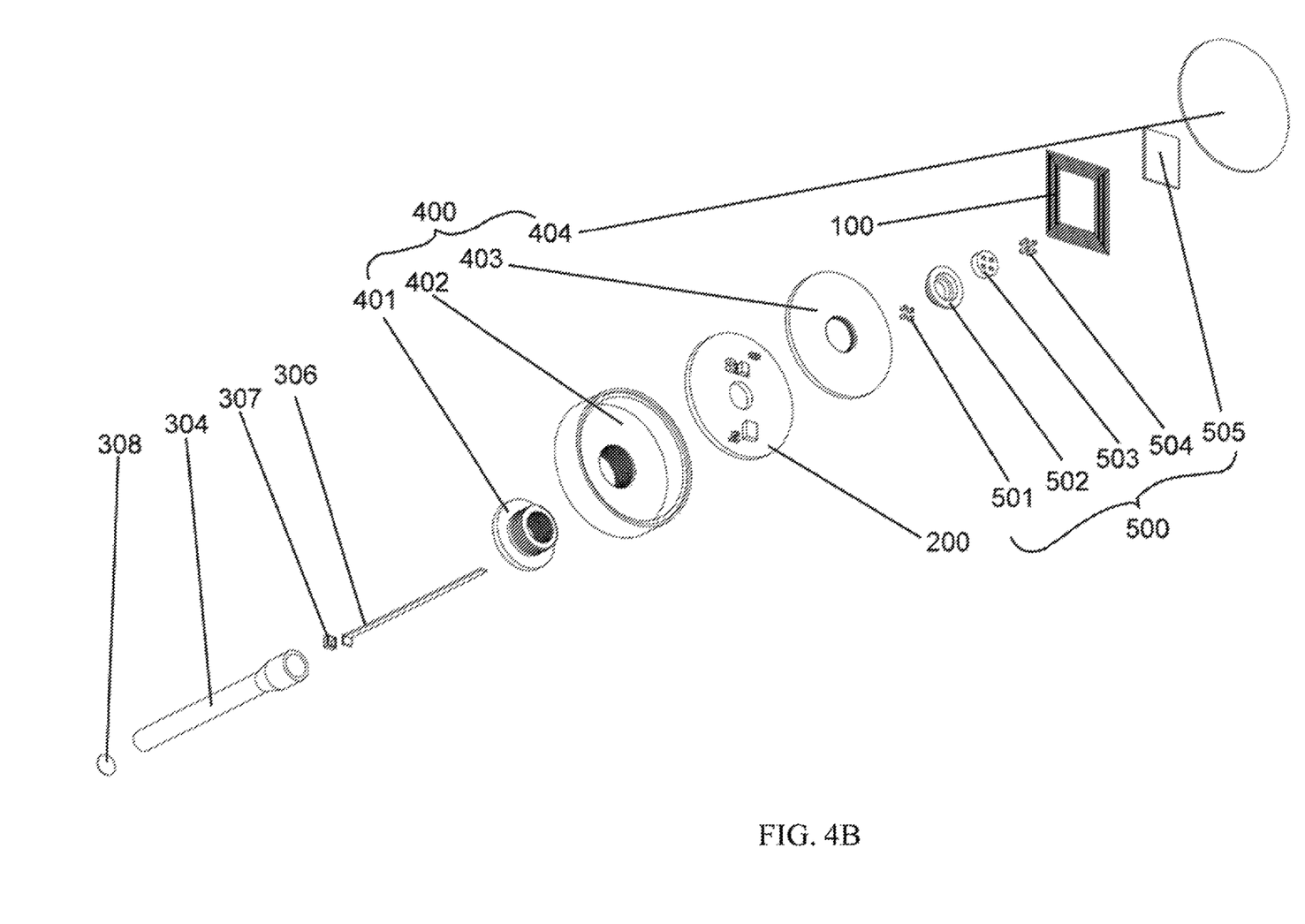
FIG. 4B is an exploded view of some embodiments of the present invention.
Figure 4C:
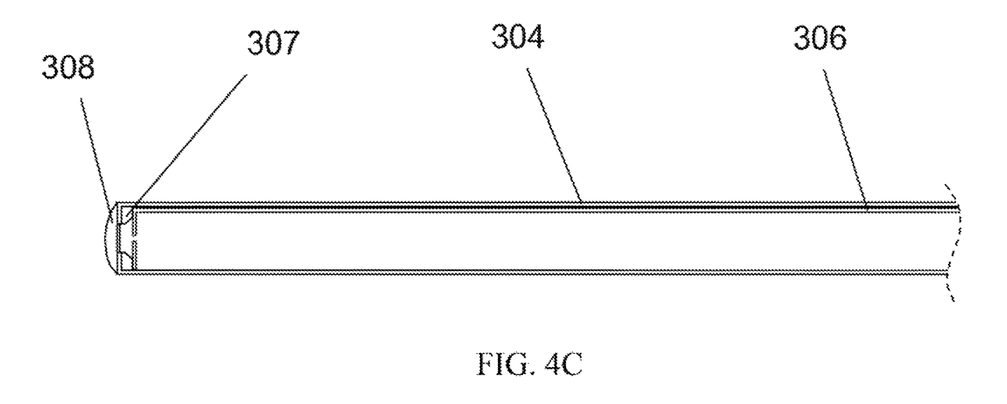
FIG. 4C is a horizontal cross-sectional view of a sensing module, in accordance with some embodiments of the present invention.
Figure 4D:
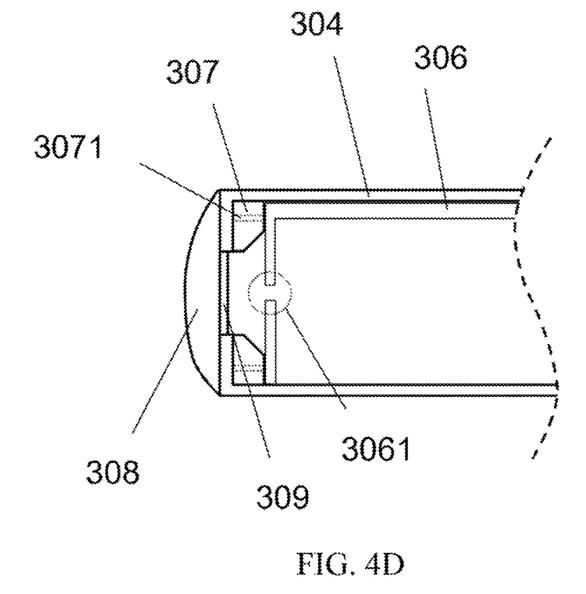
FIG. 4D is a schematic diagram illustrating the sensor region of a sensing module, in accordance with some embodiments of the present invention.

Referring to FIG. 4A-4D. FIG. 4A is a perspective view illustrating some embodiments of the present invention. FIG. 4B is an exploded view of some embodiments of the present invention. FIG. 4C is a horizontal cross-sectional view of a sensing module, in accordance with some embodiments of the present invention. FIG. 4D is a schematic diagram illustrating the sensor region of a sensing module, in accordance with some embodiments of the present invention.

As illustrated in FIGS. 4A and 4B, the overall structure of the present embodiments is similar to FIGS. 3A and 3B. One of the differences is that the pressure sensor 307 is implemented by a different method and employing a different mechanism in FIGS. 4A and 4B.

As illustrated in FIGS. 4C and FIG. 4D, the pressure sensor 307 is configured at the bottom of the internal space of the catheter 304. The pressure sensor 307 detects the deformation of a diaphragm induce by pressure and transmits the signal of detected deformation to the processing module 200 through the in-catheter wire 306. The pressure sensor 307 is connected to the in-catheter wire 306 through a through silicon via (TSV), together as a 3D integrated circuit (3D IC). Accordingly, the structure illustrated in FIG. 4D comprises a via 3071.

Similar to FIG. 3A-3D, the internal space of the catheter 304 is at atmospheric pressure. A vent hole 3061 is configured on the in-catheter wire 306 to maintain the pressure around the diaphragm 309 at atmospheric pressure. Moreover, a film 308 is configured on the diaphragm 309 to reduce the direct damages to the diaphragm 309 caused by external pressure in some embodiments.

The film 308 plays a role to pass the external pressure but prevent some direct damages applied to the diaphragm 309. The film 308 is accordingly made of, but not limited to, some materials with stronger resistance to deformation. Note that in some other embodiments, the pressure sensor 307 may be configured to detect the deformation of both the diaphragm 309 and the catheter 304 to provide more accurate results.

In still some other embodiments, the catheter 304 is an expandable tube actuated by a micro-motor or screw to adjust the depth of implantation. To maintain the internal space of the catheter 304 at atmospheric pressure, a pressure control valve may be configured on any component connected with the catheter 304 in the main body 400.

In yet some other embodiments, a temperature sensor is configured in the catheter 304 to calibrate the calculation of deformation. A microtube may expand and contract in response to external temperature, which is a type of the deformation not induced by external pressure. Accordingly, the temperature sensor is configured to provide basis to remove the part of deformation induced by temperature in the calculation.

Figure 5:
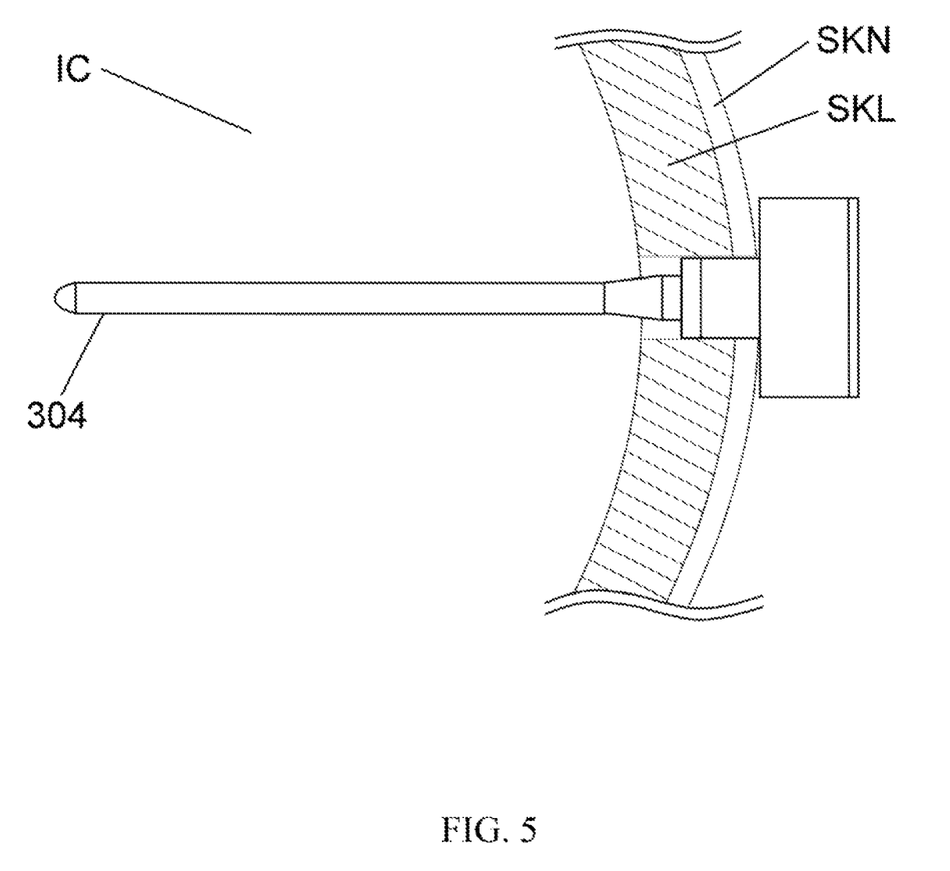
FIG. 5 is a schematic diagram illustrating a wireless intracranial pressure monitor in-use, in accordance with some embodiments of the present invention.

FIG. 5 is a schematic diagram illustrating a wireless intracranial pressure monitor in-use, in accordance with some embodiments of the present invention. As illustrated in FIG. 5, the wireless intracranial pressure monitor is configured to monitor intracranial pressure. As such, the sensing module 300 is penetrating through the skin SKN and skull SKL, and implanted into the intracranium IC to monitor the region in interest. In some embodiments, the surface of the main body 400 is decorated as a screw to ensure a firm connection between the main body 400 and the skull SKL. In some other embodiments, the surface of the main body 400 is decorated as other known means to ensure a firm connection by snatching or latching.

There are many inventions described and illustrated above. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

What is claimed is:

1. A wireless intracranial pressure monitor, comprising:
a main body;
a wireless transceiver configured in the main body;
a processing module connected to the wireless transceiver; and
a sensing module connected to the processing module, wherein the sensing module comprises:
a catheter, which is a closed tube;
a pressure sensor configured on the catheter;
wherein the pressure sensor comprises a through silicon via (TSV);
a diaphragm connected to the pressure sensor through the catheter; and
an in-catheter wire connecting the pressure sensor with the processing module;
wherein the pressure sensor is configured to detect the deformation of the diaphragm induced by pressure and is connected to the in-catheter wire through the through silicon via (TSV);
wherein an internal space of the catheter is at an atmospheric pressure, and a vent hole which is configured in the internal space of the catheter maintains the pressure around the diaphragm at the atmospheric pressure.

2. The wireless intracranial pressure monitor as claimed in claim 1, wherein the main body comprises:
an adapter connected to the catheter;
a housing connected to the adapter;

a spacer configured in the housing, wherein the spacer is configured to separate the wireless transceiver and the processing module; and a cover connected to the housing.

3. The wireless intracranial pressure monitor as claimed in claim 2, wherein the main body comprises a connector comprising:

a first wire connected to the processing module;

a first supporter connected to the spacer;

a second supporter connected to the first supporter;

a second wire penetrating the second supporter and connected to the first wire; and a supporting plate connected to the second wire and the wireless transceiver.

4. The wireless intracranial pressure monitor as claimed in claim 1, wherein the wireless transceiver is a coil.

5. The wireless intracranial pressure monitor as claimed in claim 1, wherein the pressure sensor is connected to a pressure sensing circuit regulator.

6. The wireless intracranial pressure monitor as claimed in claim 1, wherein the processing module comprises:

a microcontroller;

a RF transceiver connected to the microcontroller;

a power supply connected to the microcontroller and the RF transceiver respectively; and an analog front-end circuit connected to the microcontroller and the sensing module respectively.

7. The wireless intracranial pressure monitor as claimed in claim 1, wherein the processing module comprises:

a microcontroller connected to the sensing module;

a RF transceiver connected to the microcontroller; and a power supply connected to the microcontroller and the RF transceiver respectively.

8. The wireless intracranial pressure monitor as claimed in claim 7, wherein the microcontroller comprises:

a power-on reset configured in the microcontroller;

a programmable-gain amplifier connected to the sensing module;

an analog-to-digital converter connected to the programmable-gain amplifier;

an analog-to-digital buffer connected to the analog-to-digital converter;

a digital signal processor connected to the analog-to-digital converter;

a power management oscillator connected to the power supply and the digital signal processor;

a digital register connected to the digital signal processor; and an I2C/SPI interface connected to the RF transceiver and the digital signal processor respectively.

9. The wireless intracranial pressure monitor as claimed in claim 1, wherein the catheter is a tube made of titanium alloy.

10. The wireless intracranial pressure monitor as claimed in claim 1, wherein a film is configured on the diaphragm.

* * * * *